(12) United States Patent  
Xiliang et al.

(10) Patent No.: US 11,020,119 B2  
(45) Date of Patent: Jun. 1, 2021

(54) ANVIL ASSEMBLY AND DELIVERY SYSTEM

(71) Applicant: Covidien LP, Mansfield, MA (US)

(72) Inventors: Zhang Xiliang, Shanghai (CN); Zhaokai Wang, Shanghai (CN); Baojun Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 248 days.

(21) Appl. No.: 16/000,244

(22) PCT Filed: Dec. 7, 2015

(86) PCT No.: PCT/CN2015/096531  
§ 371 (c)(1),  
(2) Date: Jun. 5, 2018

(87) PCT Pub. No.: WO2017/096502  
PCT Pub. Date: Jun. 15, 2017

(65) Prior Publication Data  
US 2019/0083096 A1 Mar. 21, 2019

(51) Int. Cl.  
*A61B 17/24* (2006.01)  
*A61B 17/115* (2006.01)  
*A61B 17/068* (2006.01)  
*A61B 17/00* (2006.01)

(52) U.S. Cl.  
CPC ........ *A61B 17/1155* (2013.01); *A61B 17/068* (2013.01); *A61B 2017/00292* (2013.01)

(58) Field of Classification Search  
CPC ...... A61B 17/1155; A61B 2017/07257; A61B 17/24  
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Aug. 19, 2019, issued in EP Appln. No. 15909977.

(Continued)

*Primary Examiner* — Praachi M Pathak  
(74) *Attorney, Agent, or Firm* — Carter, DeLuca & Farrell LLP

(57) ABSTRACT

An anvil assembly suitable for trans-oral delivery includes an anvil head configured to be tilted. An anvil delivery assembly includes the anvil assembly and a tubular guide assembly secured to the anvil assembly. The tubular guide assembly includes a flexible tube having an oblate cross-section.

10 Claims, 4 Drawing Sheets

(56) References Cited

U.S. PATENT DOCUMENTS

| | | |
|---|---|---|
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |

(56) References Cited

U.S. PATENT DOCUMENTS

| | | |
|---|---|---|
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 * | 4/2008 | Milliman ............ A61B 17/068 227/175.1 |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 * | 2/2012 | Milliman ............ A61B 17/1114 227/175.1 |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,498,222 B2 * | 11/2016 | Scheib ............... A61B 17/1155 |
| 2003/0111507 A1 | 6/2003 | Nunez |
| 2004/0073090 A1 | 4/2004 | Butler et al. |
| 2004/0087977 A1 * | 5/2004 | Nolan ................. A61B 17/1114 606/142 |
| 2004/0195289 A1 * | 10/2004 | Aranyi ................ A61B 17/072 227/180.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0082785 A1 * | 3/2009 | Milliman ............ A61B 17/1155 606/139 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 * | 5/2013 | Mozdzierz ......... A61B 17/1155 227/175.1 |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |

(56) References Cited

U.S. PATENT DOCUMENTS

| | | |
|---|---|---|
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams ........... A61B 17/1155 227/175.1 |
| 2015/0069108 A1* | 3/2015 | Williams ........... A61B 17/1114 227/175.1 |
| 2015/0129636 A1* | 5/2015 | Mulreed ............. A61B 17/115 227/177.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0231636 A1* | 8/2017 | Williams ........... A61B 17/1155 227/179.1 |
| 2019/0298366 A1* | 10/2019 | Williams ........... A61B 17/1155 |
| 2019/0298372 A1* | 10/2019 | Guerrera ........... A61B 17/1155 |

FOREIGN PATENT DOCUMENTS

| | | |
|---|---|---|
| CN | 104207815 A | 12/2014 |
| DE | 1057729 B | 5/1959 |
| DE | 3301713 A1 | 7/1984 |
| EP | 0152382 A2 | 8/1985 |
| EP | 01473451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

OTHER PUBLICATIONS

Chinese Office Action dated Jul. 1, 2020, issued in CN Appln. No. 201580084929, 4 pages.

* cited by examiner

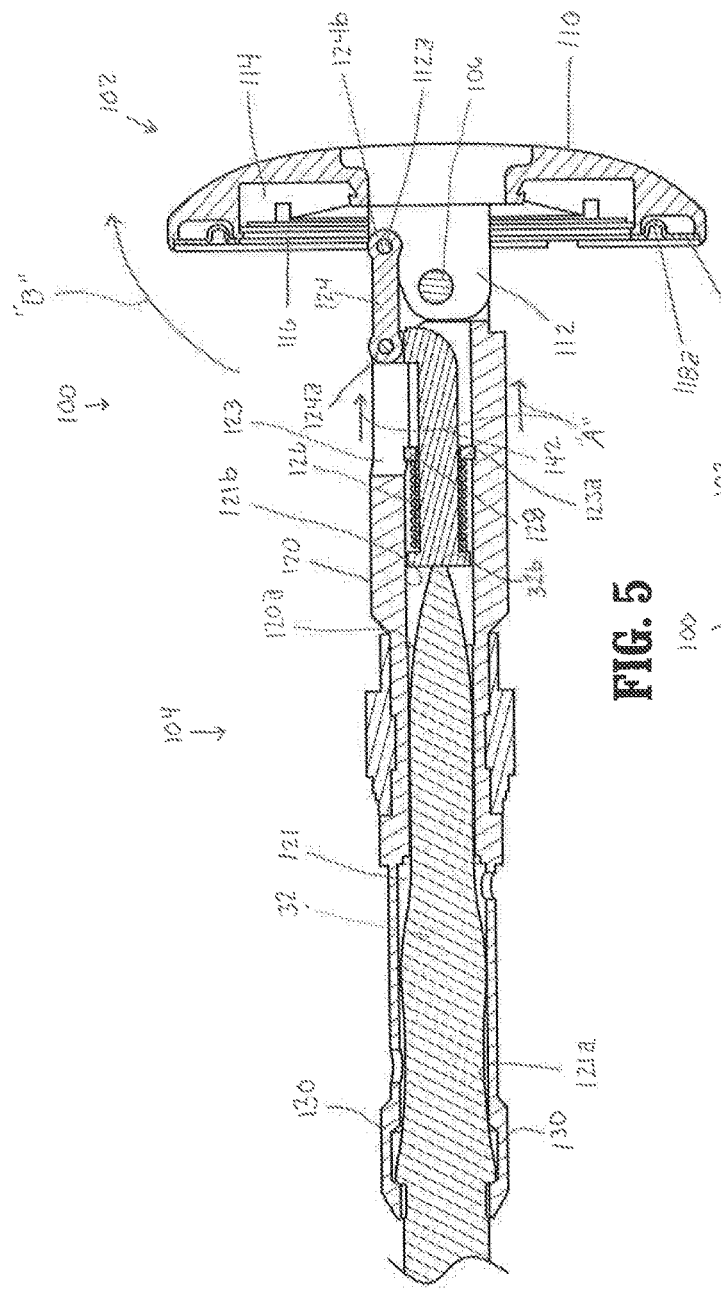
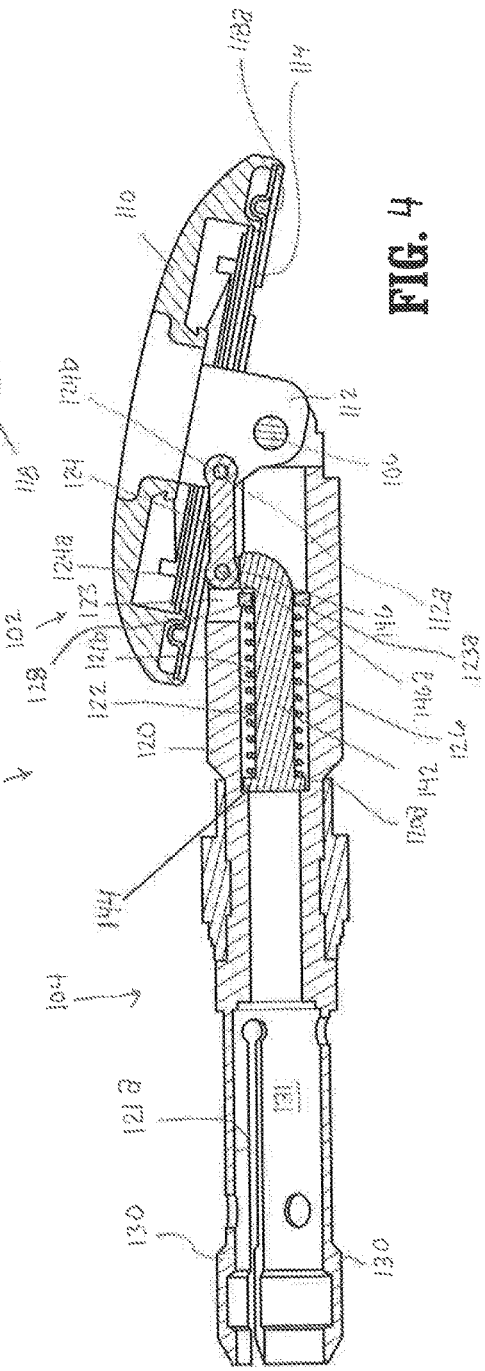

ANVIL ASSEMBLY AND DELIVERY SYSTEM

CROSS-REFERENCE TO RELATED APPLICATIONS

This application claims benefit of and priority to National Stage Application Serial No. PCT/CN2015/096531 under 35USC § 371 (a), filed Dec. 7, 2015 the disclosure of the above-identified application is hereby incorporated by reference in its entirety.

BACKGROUND

Technical Field

The present disclosure relates to an anvil assembly for use with a surgical stapling instrument. More particularly, the present disclosure relates to an anvil assembly and a system for trans-oral delivery of the anvil assembly.

Background of Related Art

Anastomosis is the surgical joining of separate hollow organ sections to allow the sections to intercommunicate with each other. Typically, an anastomosis procedure follows surgery in which a diseased or defective section of hollow tissue is removed and the remaining end sections are to be joined. Depending on the desired anastomosis procedure, the end sections of the hollow organ may be joined using circular, end-to-end, end-to-side, or side-to-side organ reconstruction methods.

In a circular anastomosis procedure, the two ends of the organ sections are joined by means of a surgical stapling instrument which drives a circular array of staples through the organ end sections and cores and removes any overlapping tissue to free a tubular passage. In some applications of a circular anastomosis procedure, an anvil rod having an attached anvil head is mounted to the distal end of a surgical stapling instrument shaft prior to insertion of the instrument into the tissue to be anastomosed. However, in other applications, a detachable anvil rod may be mounted to the instrument subsequent to positioning of the surgical stapling instrument and the anvil assembly within respective organ sections. In such instances, the surgical stapling instrument and the anvil assembly are separately delivered to the operative site. Each organ end section is then secured to a respective anvil or staple holding component, e.g., by a purse string suture. The anvil assembly is mounted to the surgical stapling instrument by inserting a mounting portion of the anvil rod within the distal end of the surgical stapling instrument so that a mounting mechanism within the surgical stapling instrument securely engages the anvil rod. Preparation of the organ sections to be joined and mounting of the anvil rod to the surgical stapling instrument may be performed using minimally invasive surgical techniques, i.e., under laparoscopic guidance.

An anvil assembly delivery system for delivering an anvil assembly trans-orally to a surgical site, e.g., the stomach, is disclosed in commonly owned U.S. Pat. No. 8,109,426, the content of which is incorporated herein by reference in its entirety. As described, the anvil assembly includes a tilting head assembly secured to the body assembly for facilitating trans-oral delivery of the anvil assembly to the surgical site.

To further facilitate trans-oral delivery of the anvil assembly to the surgical site, it would be beneficial to have an anvil assembly with a head assembly that is smaller in size. It would also be beneficial to have an anvil assembly capable of tilting to a greater degree.

SUMMARY

In accordance with the present disclosure, an anvil assembly is provided for use with a surgical stapling instrument for performing end-to-end anastomosis of tissue. The anvil assembly includes an anvil center rod defining a throughbore and a plunger member positioned within the throughbore of the anvil center rod. The plunger member is movable between a proximal position and a distal position, and a spring is received about the plunger member. The spring is positioned to bias the plunger member towards the proximal position. A head assembly is pivotally secured to the anvil center rod about a pivot axis. The head assembly is movable between a tilted position and an operative position. The plunger member is operatively connected to the head assembly to cause movement of the head assembly from the tilted position to the operative position as the plunger member moves from the proximal position to the distal position.

In embodiments, the plunger member is connected to the head assembly by a drive link. The plunger member may include an elongate body for supporting the spring and a flange on a proximal end of the elongate body for maintaining the spring about the elongate body. The plunger member may have a J-shape. The anvil assembly may further include a clip supported within the anvil center rod and about the elongate body of the plunger for further maintaining the spring about the elongate body.

Also provided is an anvil delivery system including an anvil assembly and a tubular guide assembly for trans-oral insertion of the anvil assembly. The tubular guide assembly may include a flexible tube and an adapter configured for operably connecting the flexible tube to the anvil center rod. The tubular guide assembly may further include a retaining suture for maintaining the head assembly of the anvil assembly in the tilted position. The flexible tube may include an oblate cross-section.

An anvil delivery system including an anvil assembly and a tubular guide assembly for trans-oral insertion of the anvil assembly is also provided. The anvil assembly includes an anvil center rod defining a throughbore, and a plunger member positioned within the throughbore of the anvil center rod. The plunger member is movable between a proximal position and a distal position, and a spring is positioned to bias the plunger member towards the proximal position. A head assembly is pivotally secured to the anvil center rod about a pivot axis. The head assembly is movable between a tilted position and an operative position. The plunger member is operatively connected to the head assembly to cause movement of the head assembly from the tilted position to the operative position as the plunger member moves from the proximal position to the distal position. The tubular guide assembly includes a flexible tube having an oblate cross-section.

In embodiments, the spring is received about the plunger member. The plunger member may be connected to the head assembly by a drive link. The plunger member may include a J-shape. The plunger member may include an elongate body for supporting the spring and a flange on a proximal end of the elongate body for maintaining the spring about the elongate body. The tubular guide assembly may include a retaining suture for maintaining the head assembly of the anvil assembly in the tilted position. The tubular guide assembly may include an adapter configured for operably connecting the flexible tube to the anvil center rod. The anvil assembly may further include a clip supported within the anvil center rod and about the elongate body of the plunger for further maintaining the spring about the elongate body.

BRIEF DESCRIPTION OF THE DRAWINGS

Embodiments of the presently disclosed surgical stapling instrument, anvil assembly, and anvil delivery system are described hereinbelow with reference to the drawings wherein:

FIG. 4 is a side cross-sectional view of the anvil assembly shown in FIG. 2, with a head assembly in a first or tilted position;

FIG. 5 is a side cross-sectional view of the anvil assembly shown in FIG. 4 secured to a trocar assembly, with the head assembly in a second or operative position;

DETAILED DESCRIPTION OF THE DRAWINGS

Figure 1:
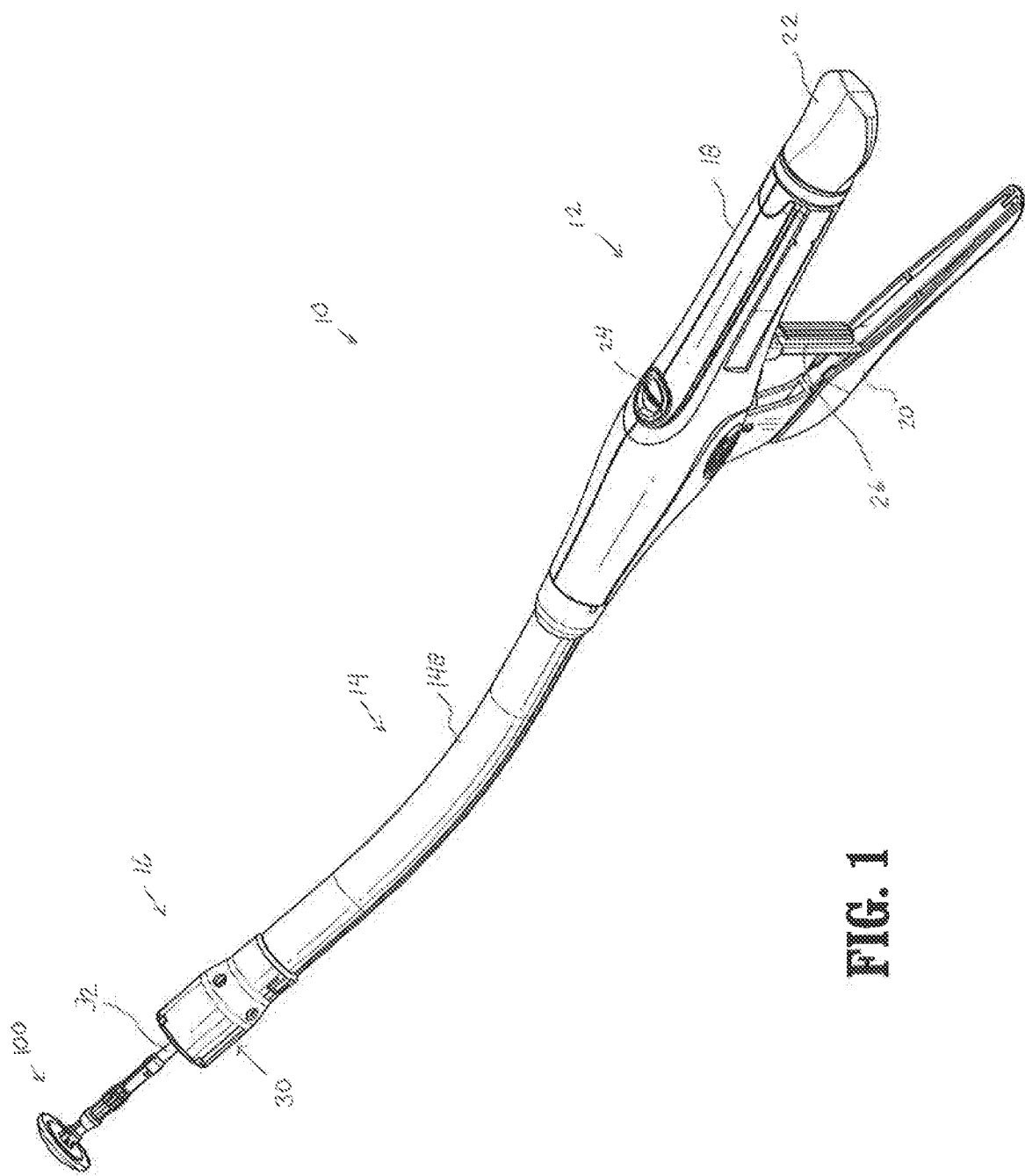
FIG. 1 is a top side perspective view from the proximal end of the presently disclosed surgical stapling instrument in the unapproximated position.

Embodiments of the presently disclosed surgical stapling instrument, anvil assembly, and anvil delivery system will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring to FIG. 1, a surgical stapling instrument including an anvil assembly according to the present disclosure is shown generally as stapling device 10. Briefly, stapling device 10 includes a proximal handle assembly 12, an elongated central body portion 14 including a curved elongated outer tube 14a, and a distal head portion 16. Handle assembly 12 includes a stationary handle 18, a firing trigger 20, a rotatable approximation knob 22, and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 100 and a shell assembly 30. The anvil assembly 100 is releasably secured to a trocar member 32 extending through the shell assembly 30. The structure and function of stapling device 10 will only be described to the extent necessary to fully disclose the aspects of the present disclosure. For a detailed description of an exemplary stapling device, please refer to commonly owned U.S. Pat. No. 7,364,060, ("the '060 patent") the content of which is incorporated herein by reference in its entirety.

Figure 2:
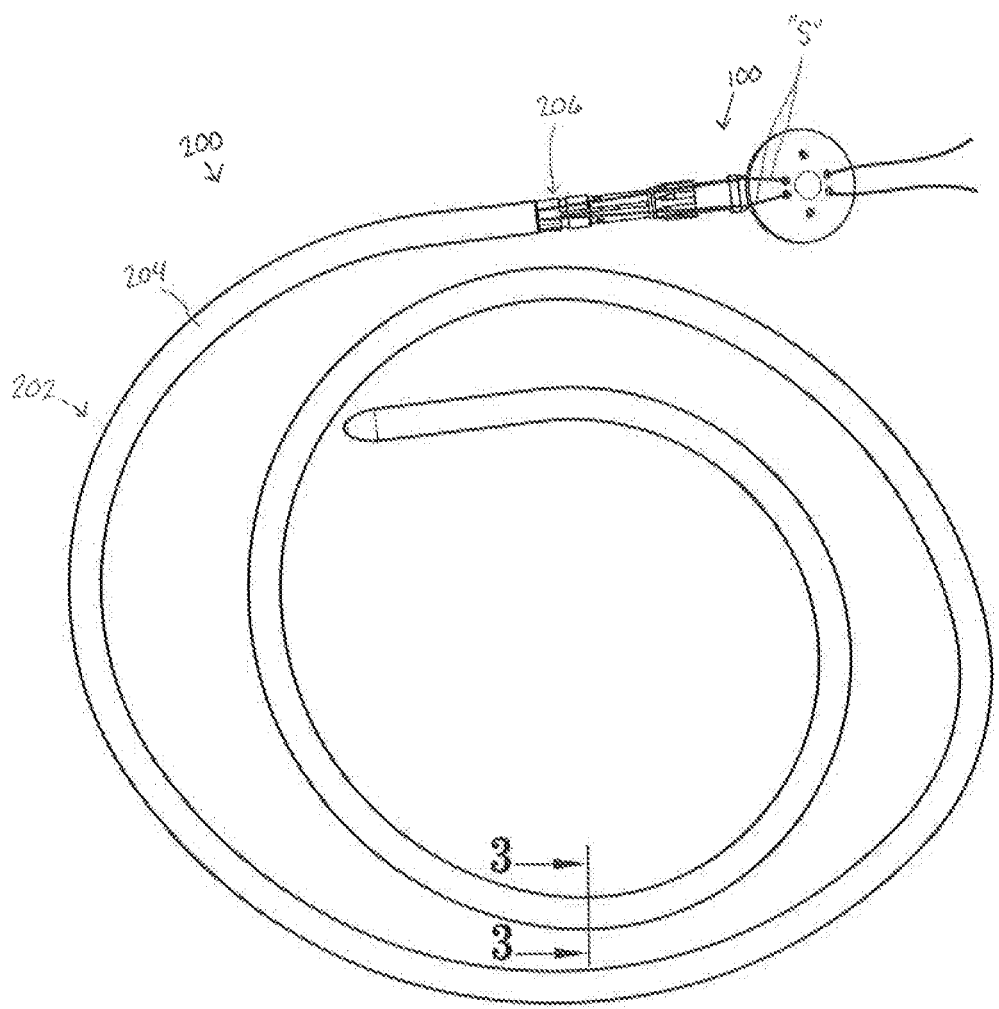
FIG. 2 is a top side perspective view of an anvil assembly of the surgical stapling instrument shown in FIG. 1 secured to an anvil delivery system.

With reference now to FIG. 2, the anvil assembly 100 is shown operably connected to a system for delivering the anvil assembly 100 within a patient, shown generally as, anvil delivery system 200. Briefly, the anvil delivery system 200 includes a tubular guide assembly 202 releasably secured to the anvil assembly 100 to facilitate trans-oral positioning of the anvil assembly 100 within a patient. More particularly, the tubular guide assembly 202 includes a flexible tube 204 which is releasably secured to the anvil assembly 100 with an adapter 206. The anvil delivery system 200 may optionally include a suture guide assembly (not shown) releasably secured to the anvil assembly 100 for manipulating the anvil assembly 100 during trans-oral delivery of the anvil assembly 100 within a patient.

With continued reference to FIG. 2, the tubular guide assembly 202 is configured to be manually detached from the anvil assembly 100 prior to attachment of the anvil assembly 100 to the stapling device 10 (FIG. 1). The anvil delivery system 200 will only be described to the extent necessary to fully disclose the aspects of the present disclosure. For a detailed description of an exemplary tubular guide assembly including a flexible tube and an adapter, please refer to commonly owned U.S. Pat. No. 8,109,426 ("the '426 patent"), the content of which is incorporated by reference herein in its entirety.

Figure 3:
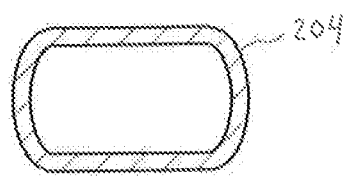
FIG. 3 is a cross-sectional end view taken along section line 3-3 shown in in FIG. 2.

Traditional delivery systems (not shown) typically include a flexible tube (not shown) including a circular cross-section. Turning to FIG. 3, embodiments of the flexible tube 202 of the tubular guide assembly 200 include an oblate cross-section. The oblate cross-section of the flexible tube 202 enables a clinician to determine the orientation of a head assembly 102 of the anvil assembly 100 simply by visualizing the flexible tube 202 during delivery of the anvil assembly 100 to a surgical site. The oblate cross-section also facilitates manipulating the anvil assembly 100 during delivery of the anvil assembly 100.

Figure 6:
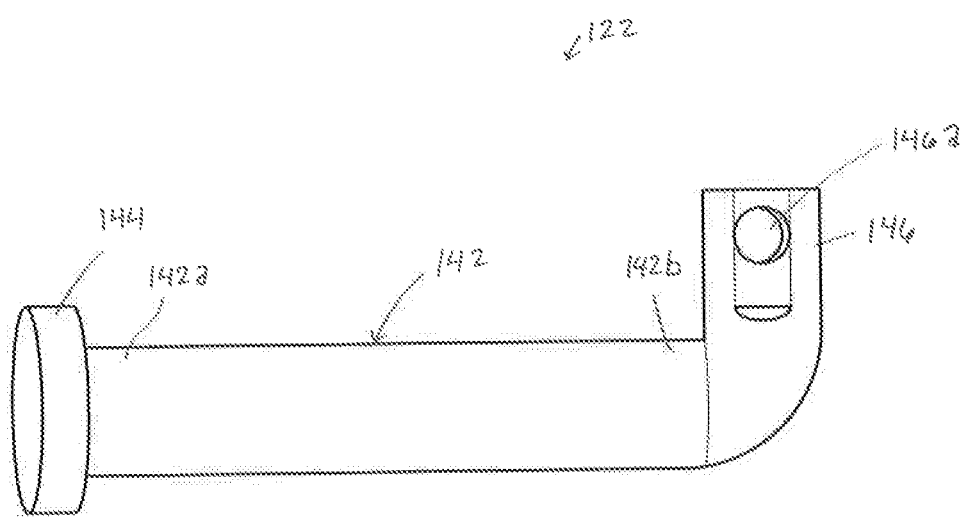
FIG. 6 is an enlarged side perspective view of a plunger member of the anvil assembly shown in FIGS. 4 and 5.

Referring now to FIGS. 4-6, as noted above, the anvil assembly 100 is configured for releasable attachment to stapling device 10 (FIG. 1). The anvil assembly 100 includes a head assembly 102 that is pivotally secured to the center rod assembly 104. The head assembly 102 is movable between a first or tilted position (FIG. 4) and a second or operative position (FIG. 5) in response to the attachment of the anvil assembly 100 to the trocar member 32 as described in detail below. The anvil assembly 100 will only be described to the extent necessary to disclose the aspects of the present disclosure. For a detailed description of exemplary anvil assemblies, please refer to the '060 and '426 patents, which were previously incorporated by reference herein in their entireties.

In embodiments, the head assembly 102 includes an anvil head 110, an anvil post 112 extending proximally from the anvil head 110, a cutting ring/backup member 114 for receiving a circular knife (not shown) of the surgical stapler 10 (FIG. 1), a cover 116 received over the cutting ring/backup member 114, and an anvil plate 118 secured to the anvil head 110 and defining staple forming pockets 118a. The anvil post 112 may be integrally formed with the anvil head 110, e.g., monolithic, or secured to the anvil head 110 through fiction fit, crimping, welding, or in any suitable manner. A pivot member 112a extends outwardly from the anvil post 112 for receiving a distal end 124b of a link member 124 of the center rod assembly 104.

The center rod assembly 104 of the anvil assembly 100 includes an anvil center rod 120, a plunger member 122 slidably supported within the anvil center rod 120, the drive link 124 for connecting the plunger member 122 to the head assembly 102 of the anvil assembly 100, a spring or biasing member, e.g., coil spring 126, received about the plunger member 122 for biasing the plunger member 122 in a proximal direction, and a clip member, i.e., U-shaped clip 128, received about the plunger member 122 for maintaining the spring 126 about the plunger member 122. The head assembly 102 is pivotally secured to the center rod assembly 104 by a pivot pin 106.

The anvil center rod 120 includes a plurality of flexible arms 130 which define a proximal end 121a of a throughbore 121 of the anvil center rod 120. The proximal end 121a of the throughbore 121 is configured to releasably receive the trocar member 32 (FIG. 5) of the surgical stapling device 10 (FIG. 1). A distal end 121b of the throughbore 121 of the anvil center rod 120 receives the plunger member 122 and the spring member 126 which is received about the plunger member 122. The anvil center rod 120 further defines a longitudinal opening 123 in communication with the distal end 121b of the throughbore 121 that receives and facilitates movement of the drive link 124 as the head assembly 110 moves between the tilted and operative positions, as described in detail below.

With particular reference to FIG. 6, the plunger member 122 of the center rod assembly 104 includes an elongate body 142 having an annular flange 144 on a proximal end 142a of the elongate body 142 and an extension 146 extending radially outward from a distal end 142b of the elongate body 142 providing the plunger member 122 with a substantially J-shaped appearance. The elongate body 142 of the plunger member 122 supports the spring member 126 such that the spring member 126 is in engagement with the annular flange 144 and positioned about the elongate body 142. The radial extension 146 of the plunger member 122 is received through the longitudinal opening 123 in the anvil center rod 120 when the plunger member 122 is received within the distal end 121b of the throughbore 121. The extension 146 includes a pivot member 146a for pivotally connecting the radial extension 146 of the plunger member 122 to a proximal end 124a of the drive link 124. As described above, the radial extension 146 and the drive link 124 are movably received within the slot 123 of the anvil center rod 120.

As will be described in further detail below, the anvil center rod 120 and the annular flange 144 of the plunger member 122 may provide an audible and/or tactile feedback to a clinician during use to indicate that the head assembly 110 of the anvil assembly 100 has returned to the tilted position (FIG. 4). The feedback may be audible and produced when the annular flange 144a of the plunger member 122 engages an inner surface 120a (FIGS. 5 and 6) of the anvil center rod 120.

Referring again to FIGS. 4 and 5, the plunger member 122 of the center rod assembly 104 and the spring member 126 are received within the distal end 121b of the throughbore 121 of the anvil center rod 120. When the plunger 122 is received within the throughbore 121, the extension 146 of the plunger member 122 extends outwardly from distal end 121b of the throughbore 121 through the longitudinal opening 123 of the anvil center rod 120. The U-shaped clip 128 is received about the plunger member 122 and is supported within an annular recess 123a of the anvil center rod 120 to maintain plunger member 122 within the throughbore 121, and to maintain the spring member 126 about the elongate body 140 of the plunger member 122. An opening (not shown) in the U-shaped clip 128 permits longitudinal movement of the elongate body 140 of the plunger member 122 therethrough and within the distal end 121b of the through-bore 121. When the head assembly 102 of the anvil assembly 100 is moved to the operative position (FIG. 5), the spring member 126 is compressed between the annular flange 144 of the plunger member 122 and the U-shaped clip 128 to bias the plunger member 122 to a proximal position.

The proximal end 124a of the drive link 124 of the center rod assembly 104 is secured to the pivot member 146a of the extension 146 of the plunger member 122 and the distal end 128b of the drive link 124 is secured to the pivot member 112a of the anvil post 112 of the head assembly 102. As noted above, the drive link 124 is configured to effect pivoting of the head assembly 102 relative to the center rod assembly 104 between the tilted position (FIG. 4) and the second or operative position (FIG. 5). The configuration of the anvil assembly 100 is such that the head assembly 102 is able to tilt to a greater degree than traditional anvil assemblies (not shown). More particularly, the longitudinal opening 123 of the anvil center rod 120 extends through a distal end of the anvil center rod 120 to accommodate the drive link 124 and a portion of the head assembly 102 when the head assembly 102 is in the tilted position.

The operation of anvil assembly 100 will now be described with reference to the figures. Referring initially to FIG. 4, the head assembly 102 of the anvil assembly 100 is shown in the first or tilted position. When the head assembly 102 is in the tilted position, the plunger member 122 of the center rod assembly 104 is in a proximal-most position within the distal end 121a of the throughbore 121 of the anvil center rod 120. The spring member 126 is received about the elongate body 142 of the plunger member 122 between the annular flange 144 and the U-shaped clip 128 and is in an expanded condition to pull the drive link 124 proximally within the slot 123 to pivot the head assembly 102 to the tilted position.

The anvil assembly 100 is secured to the anvil delivery system 200 (FIG. 2) by a suture "S" (FIG. 2) received through the head assembly 102 of the anvil assembly 100, and secured between the adapter 206 and the flexible tube 204 of the tubular guide assembly 202 of the anvil delivery system 200.

With reference now to FIG. 5, the anvil assembly 100 is shown releasably received on the trocar member 32 of the surgical device 10 (FIG. 1). In particular, the distal end of the trocar member 32 is received within throughbore 121 of the anvil center rod 120. A distal end 32b of the trocar member 32 engages a proximal end of the elongate body 142 of the plunger member 122 when the trocar member 32 is received within the throughbore 121 of the anvil center rod 120. The trocar member 32 overcomes the bias of the spring member 126 to move the plunger member 122 distally, as indicated by arrow "A" in FIG. 5, from the proximal-most position (FIG. 4) to the distal-most position (FIG. 5). As the plunger member 122 moves distally within the distal portion 121b of the throughbore 121 of the anvil center rod 120, engagement between the drive link 124 of the center rod assembly 104 and the head assembly 102 causes the head assembly 102 to pivot, as indicated by arrow "B" in FIG. 5, from the tilted position (FIG. 4) to the second or operative position (FIG. 5). Distal movement of the plunger member 122 also causes compression of the spring member 126.

Once in the operative position, the anvil assembly 100 operates similar to a traditional anvil assembly (not shown). Following a surgical stapling procedure using surgical device 10 and anvil assembly 100, the anvil assembly 100 is separated from the trocar member 32 of the surgical device 10. As the trocar member 32 is retracted from within the throughbore 121 of the anvil center rod 120 of the center rod assembly 104, the spring member 126, having been compressed during distal movement of the plunger member 122, causes the plunger member 122 to move proximally to the proximal-most position (FIG. 4), thereby returning the head assembly 102 to the first or tilted position.

As noted above, the anvil center rod 120 and the flange 144 of the plunger member 122 may be configured to provide an audible and/or tactile indication to the clinician that the plunger member 122 is in its proximal-most position, and thus, the head assembly 102 of the anvil assembly 100 is in the tilted position (FIG. 4). In this manner, the clinician is able to determine the position of the head assembly 102 relative to the center rod assembly 104 without viewing the head assembly 102 of the anvil assembly 100. The anvil assembly 100 may then be removed from the surgical site and the surgical procedure may be completed in a traditional manner.

Figure 7:
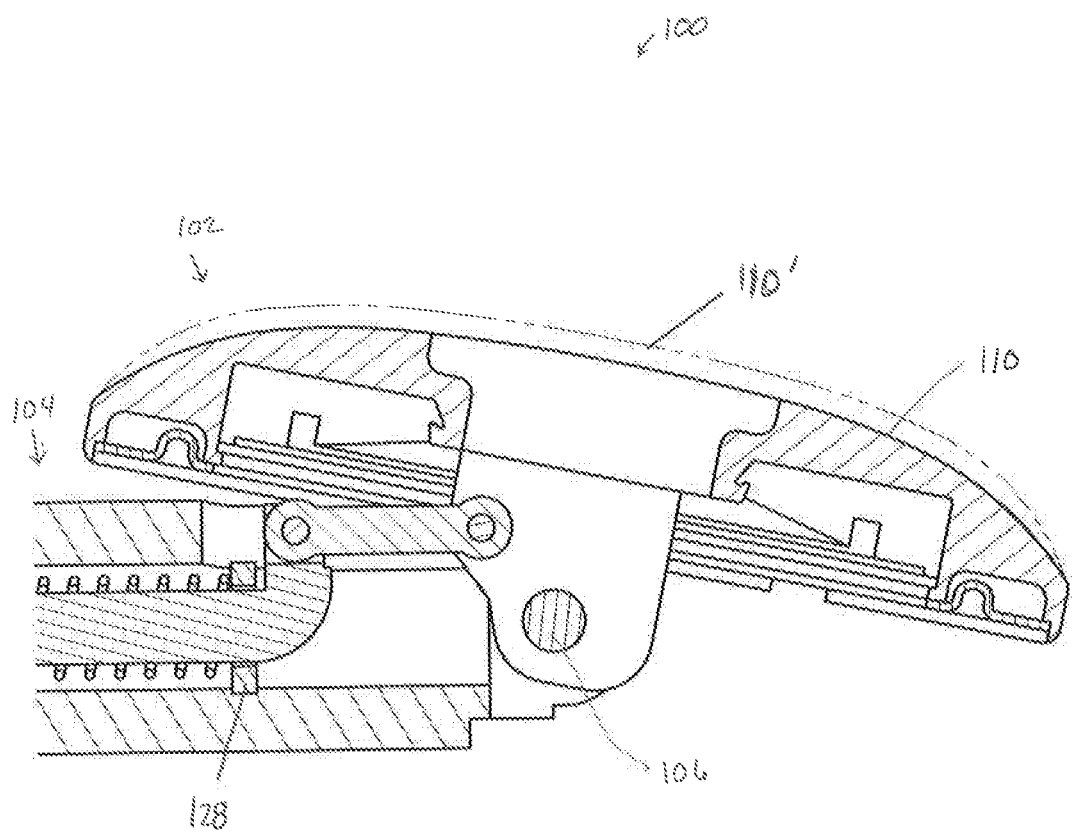
FIG. 7 is an enlarged side perspective view of the head assembly shown in FIGS. 4 and 5, including the outline of a traditional head assembly shown in phantom.

With reference now to FIG. 7, to reduce a projected area size of the head assembly 102 of the anvil assembly 100 and to further facilitate trans-oral delivery of the anvil assembly 100, the anvil head 110 of the head assembly 102 may include a modified profile. The outline of a traditional anvil head 110' of a traditional anvil assembly (not shown) is shown in phantom. As shown in FIG. 7, the anvil head 110 includes a shallower and smoother profile. It is envisioned that other modifications may be made to the anvil head 110 of the anvil assembly 100 to further reduce the projected area size of the head assembly 102 and to further facilitate trans-oral delivery of the anvil assembly 100.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
   an anvil center rod defining a throughbore;
   a plunger member positioned within the throughbore of the anvil center rod and movable between a proximal position and a distal position;
   a spring received about the plunger member, the plunger member extending entirely through the spring and the spring being positioned to bias the plunger member towards the proximal position; and
   a head assembly pivotally secured to the anvil center rod about a pivot axis, the head assembly movable between a tilted position and an operative position, wherein the plunger member is operatively connected to the head assembly to cause movement of the head assembly from the tilted position to the operative position as the plunger member moves from the proximal position to the distal position.

2. The anvil assembly of claim 1, wherein the plunger member is connected to the head assembly by a drive link.

3. The anvil assembly of claim 1, wherein the plunger member includes an elongate body configured to support the spring and a flange on a proximal end of the elongate body configured to maintain the spring about the elongate body.

4. The anvil assembly of claim 1, wherein the plunger member includes a J-shape.

5. The anvil assembly of claim 1, wherein the spring includes a distal end, the distal end of the spring being fixed within and relative to the anvil center rod.

6. An anvil assembly comprising:
   an anvil center rod defining a throughbore;
   a plunger member positioned within the throughbore of the anvil center rod and movable between a proximal position and a distal position;
   a spring received about the plunger member, the plunger member extending entirely through the spring and the spring being positioned to bias the plunger member towards the proximal position;
   a head assembly pivotally secured to the anvil center rod about a pivot axis, the head assembly movable between a tilted position and an operative position, wherein the plunger member is operatively connected to the head assembly to cause movement of the head assembly from the tilted position to the operative position as the plunger member moves from the proximal position to the distal position, the plunger member including an elongate body configured to support the spring and a flange on a proximal end of the elongate body configured to maintain the spring about the elongate body; and
   a clip supported within the anvil center rod and about the elongate body of the plunger member, the clip configured to maintain the spring about the elongate body.

7. An anvil delivery system comprising:
   an anvil assembly as recited in claim 1; and
   a tubular guide assembly for trans-oral insertion of the anvil assembly.

8. The anvil delivery system of claim 7, wherein the tubular guide assembly includes a flexible tube and an adapter configured to operably connect the flexible tube to the anvil center rod.

9. The anvil delivery system of claim 8, wherein the tubular guide assembly further includes a retaining suture positioned to maintain the head assembly of the anvil assembly in the tilted position.

10. The anvil delivery system of claim 8, wherein the flexible tube includes an oblate cross-section.

* * * * *